| United States Patent [19] | [11] 4,234,737 |
|---|---|
| Photis | [45] Nov. 18, 1980 |

[54] PROCESS FOR PREPARING THIENYLGLYOXYLIC ACIDS AND AMIDES

[75] Inventor: James M. Photis, Ridgefield, Conn.

[73] Assignee: Stauffer Chemical Company, Westport, Conn.

[21] Appl. No.: 42,487

[22] Filed: May 25, 1979

[51] Int. Cl.³ .................... C07D 333/24; A61K 31/38
[52] U.S. Cl. ...................................... 549/70; 424/275
[58] Field of Search ................................... 549/70, 71

[56] References Cited

PUBLICATIONS

Wagner et al., "Synthetic Org. Chem.," (1965), p. 595.
Hartough, "Thiophene & its Deriv.," (1952), p. 382.

Primary Examiner—Alan Siegel
Attorney, Agent, or Firm—William C. Gerstenzang

[57] ABSTRACT

Thienylglyoxylic acids and/or amides thereof are prepared by reacting thiophene carboxylic acid chloride with sodium cyanide and hydrolyzing the resulting product in a strong mineral acid.

9 Claims, No Drawings

PROCESS FOR PREPARING THIENYLGLYOXYLIC ACIDS AND AMIDES

BACKGROUND OF THE INVENTION

The present invention relates to a process for the preparation of thienylglyoxylic acids and thienylglyoxamides. More particularly, the present invention relates to a phase transfer catalyzed process for the preparation of thienylglyoxylic acids and thienylgloxamides.

Thienylglyoxylic acids and their amides are very important industrial raw materials which are used in the preparation of many antibacterial pharmaceuticals. Thus, for example, 2-thienylglyoxylic acid may easily be converted to an alpha amino thiophene acetic acid as follows:

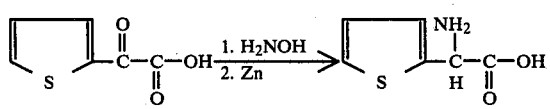

or to an alpha-hydroxythiopheneacetic acid as follows:

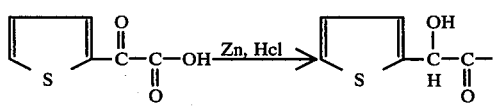

These latter compounds may be used to prepare various cephalosporin compounds which are useful antibacterial drugs, as follows:

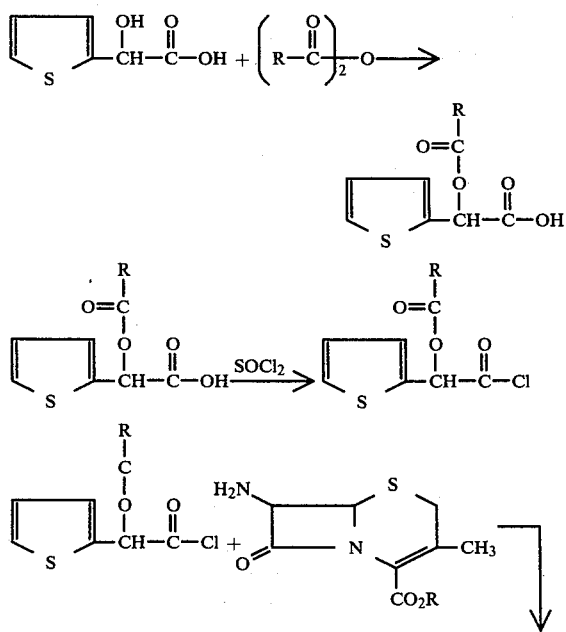

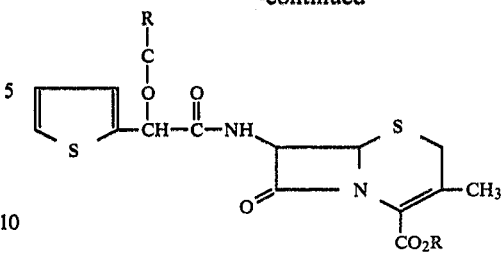

Other important pharmaceutical compounds which can be prepared from thienylglyoxylic acid are thiopheneacetic acid esters. These compounds can be prepared as follows:

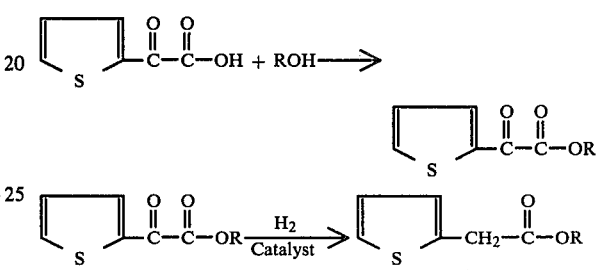

In the absence of a convenient source of thienylglyoxylic acid, these compounds would normally be prepared by the more tedious route of chloromethylating thiophene to form thienyl chloride, then reacting the thienyl chloride with sodium cyanide to form the thienyl cyanide and finally hydrolyzing and, in the case of the ester, esterifying.

Thienylglyoxylic acids are generally prepared by reacting thiophene with acetyl chloride to form acetyl thiophene, and then oxidizing to form the acid, as follows:

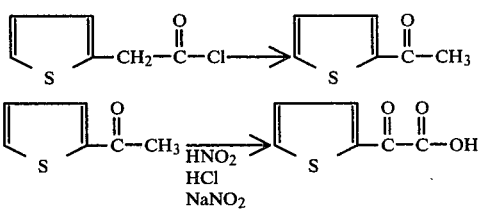

It is generally understood, however, that whenever nitrous acid is reacted with organic compounds, a possibility exists that nitroso compounds, which are suspected carcinogens, may be formed as by-products.

Therefore a need exists for a new process for the preparation of thienylglyoxylic acids and amides.

SUMMARY OF THE INVENTION

It is an object of the present invention to provide an alternative process for the preparation of thienylglyoxylic acid which process may also be employed to produce the amides thereof.

This and other objects are met by a process for preparing thienylglyoxylic acids and amides wherein thiophenecarboxylic acid chloride is converted to the thiophenecarboxylic acid cyanide by a phase transfer catalyzed reaction with sodium cyanide, and the thiophenecarboxylic acid cyanide is then hydrolyzed to form the glyoxamide; which can be further hydrolyzed to form the acid.

DETAILED DESCRIPTION OF THE INVENTION

In accordance with the present invention there is provided a process for preparing thienylglyoxyl compounds selected from the group consisting of thienylglyoxylic acids, thienylglyoxamides and mixtures thereof which comprises reacting a thiophene carboxylic acid chloride with aqueous sodium cyanide in an inert water-immiscible solvent and in the presence of a phase transfer catalyst to form a thiophene carboxylic acid cyanide, and reacting the thiophene carboxylic acid cyanide with a strong mineral acid at a temperature and for a time sufficient to form at least one compound selected from the group consisting of thienylglyoxylic acids and thienylgloxamides.

The thiophene carboxylic acid chloride employed as a starting material in the process of the present invention is represented by the structural formula:

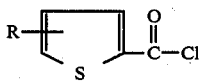

wherein R represents hydrogen, a halogen, an alkyl group having from 1 to about 8 carbon atoms, a cycloalkyl group having from 1 to about 8 carbon atoms or any combination thereof.

The phase transfer catalysts which are employed in the process of the present invention can be any of those which are useful for this type of reaction. These include, but are not limited to, quaternary ammonium salts which are soluble in both the aqueous and organic phases, such as benzyl trimethyl ammonium chloride,
tetra-n-butyl ammonium bromide,
tetra-n-butyl ammonium iodide and
tetra-n-hexyl ammonium bromide; although tetra-n-butyl ammonium bromide and tetra-n-butyl ammonium iodide are preferred; with tetra-n-butyl ammonium bromide being most preferred. Other types of phase transfer catalysts may also be used.

The process of the present invention may be illustrated as follows:

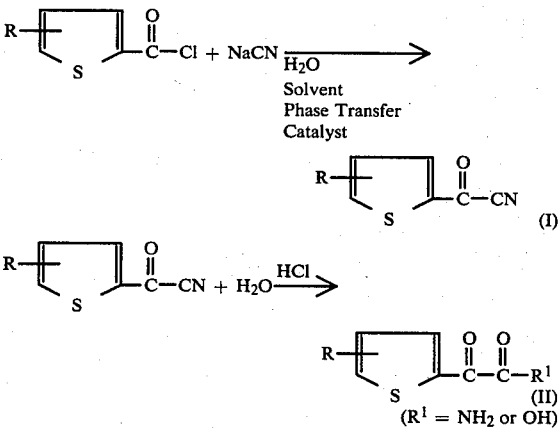

The process of the present invention is effective in preparing thienylglyoxamide, thienylglyoxylic acid, or mixtures thereof, depending on the degree of completion to which reaction II is permitted to progress.

Thus, reaction II may be further analyzed as involving reactions IIA and IIB as follows:

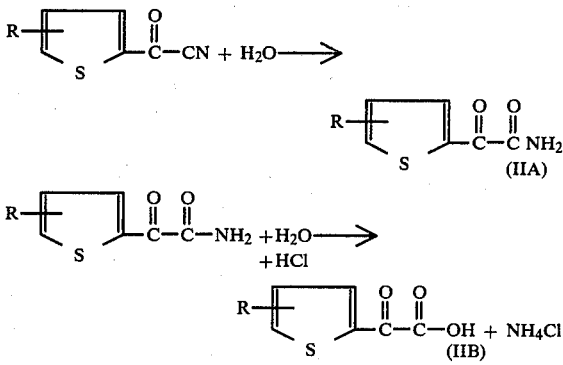

Reaction IIA is generally substantially completed in accordance with the process of the present invention, in about two hours. Reaction IIB, on the other hand, is generally substantially completed in from about eight to about sixteen hours.

Therefore, in accordance with one preferred embodiment of this invention there is provided a process for preparing thienylglyoxylic acid which comprises reacting thiophene carboxylic acid chloride with aqueous sodium cyanide in a water-immiscible solvent and in the presence of a phase-transfer catalyst to form thiophene acyl cyanide, and then reacting the thiophene acyl cyanide with a strong mineral acid at a temperature and for a time sufficient to form thienylglyoxylic acid.

In accordance with another preferred embodiment of the invention, there is provided a process for preparing thienylglyoxamide which comprises reacting thiophene carboxylic acid chloride with aqueous sodium cyanide in a water-immiscible solvent and in the presence of a phase transfer catalyst to form thiophene carboxylic acid cyanide and reacting the thiophene carboxylic acid cyanide with a strong mineral acid at a temperature and for a time sufficient to form thienylglyoxamide.

It is surprising and unexpected that when thiophene carboxylic acid chloride is reacted with aqueous sodium cyanide under conditions of phase-transfer catalysts no dimer product is produced. Thus, it is well-known that when benzoyl chloride is reacted under similar conditions, the resulting product contains up to about 50% dimer. It is also surprising and unexpected that when the thiophene carboxylic acid cyanide is reacted with a strong mineral acid the α-keto-product is formed. Conventional technology would have predicted that the cyano group would be cleaved and a carboxylic acid formed.

In practicing the process of the present invention a solution of thiophene carboxylic acid chloride and a phase transfer catalyst in an inert water-immiscible solvent is prepared. The concentration of thiophene carboxylic acid chloride can range from about 5% to about 25% by weight of solvent, with concentrations ranging from about 15 to about 20 weight % being preferred.

There are many solvents known in the art which can be used as the inert water-immiscible solvents in the practice of the present invention. These include, but are not limited to methylene chloride and other halogenated hydrocarbons; aliphatic hydrocarbons, aromatic hydrocarbons and ether solvents; although methylene chloride is preferred.

The amount of phase transfer catalyst employed will vary in accordance with many wellunderstood factors, including the characteristics of the particular phase transfer catalyst employed. When using the preferred phase transfer catalysts of the present invention, such as tetra-n-butyl ammonium iodide or bromide, concentrations ranging from about 0.005% to about 1.0% by weight of solvent are used; although concentrations ranging from about 0.1% to 0.3% by weight of solvent are preferred.

An aqueous solution of sodium cyanide is then stirred into the solution to form a two-phase reaction mass. The concentration of sodium cyanide in the aqueous sodium cyanide solution ranges from about 15% to about 25% by weight of solution. The aqueous sodium cyanide is added to the solution in an amount sufficient to supply a stoichiometric amount of sodium cyanide for reaction with the thiophene carboxylic acid chloride. A greater amount may be used without any significant adverse consequences.

The ensuing reaction is exothermic and external cooling will generally be required. The external cooling is generally used to control the reaction temperature at refluxing temperature or less; although refluxing temperature is preferred. The essential completion of this first reaction (illustrated schematically as I above) will be indicated by the disappearance of the acid chloride carbonyl absorption band in the infrared spectrum, which will generally have occurred about 15 to 20 minutes after the reaction has been initiated.

The water-immiscible phase is then separated from the reaction mass, and the solvent evaporated to separate the thiophene carboxylic acid cyanide product.

The thiophene carboxylic acid, which is a solid, can then by hydroxyzed with a strong mineral acid, such as hydrochloric acid (i.e., about 37% weight HCl) to form thienylglyoxamide, thienyl glyoxylic acid or mixtures thereof. This final product or product mixture is then separated out by water dilution and crystallization or solvent extraction.

The ultimate product formed (i.e., thienylglyoxamide, thienylglyoxylic acid or mixtures thereof) is determined by the degree to which the hydrolysis reaction is permitted to go to completion. This, in turn, is determined by the temperature at which the hydrolysis is conducted and the length of time it is permitted to proceed. Thus, for example, if the hydrolysis reaction is conducted at a temperature ranging from about 10° C. to about 40° C. and permitted to proceed for about two hours, a product which is essentially all thienylglyoxamide will generally be formed.

If, on the other hand, the hydrolysis is conducted at a temperature ranging between about 20° C. and about 60° C. and permitted to proceed for about 16 hours, a product which is essentially all thienylglyoxylic acid will generally be formed; if conducted at a temperature ranging from about 10° C. to about 40° C. and permitted to proceed for a period of time ranging between about 2 hours and about 16 hours, a mixture of thienylglyoxamide and thienylglyoxylic acid can be formed.

The hydrolysis is accomplished through the use of a strong mineral acid, preferably in concentrated form. Typical of the strong mineral acids which can be used are hydrochloric, sulfuric, nitric and phosphoric acids, although hydrochloric acid and sulfuric acid are preferred, and hydrochloric acid is especially preferred.

In order that the present invention be more fully understood, the following examples are given by way of illustration. No specific details or enumerations contained therein should be construed as limitations except insofar as they appear in the appended claims. All parts and percentages are by weight unless otherwise specifically designated.

EXAMPLE I

2-THIENYLGLYOXAMIDE

An aqueous solution of sodium cyanide (60 g, 1.2 moles) in 220 milliliters of water was mixed with a magnetically stirred solution of 2-thiophene carboxylic acid chloride (147.5 g, 1.0 mole) in 500 milliliters of methylene chloride containing 1.0 g of tetra-n-butylammonium bromide. An exothermic reaction took place. Cooling was necessary to prevent the solvent from boiling due to the exothermicity of the reaction. After about ten minutes the exotherm subsided, and the methylene chloride layer was then separated. Infrared analysis revealed a single carbonyl absorption at 1660 cm$^{-1}$ and a sharp $\gamma_{CN}$ absorption at 2220 cm$^{-1}$. The solvent was removed under reduced pressure. Concentrated hydrochloric acid (500 milliliters) was added to the mixture and the whole was mechanically stirred. The temperature began to increase and cooling was applied to keep the reaction mass at a temperature below about 40° C. After about two hours the solids had completely dissolved. Water (about 1 liter) was added and the solution was chilled. A crystalline solid was formed, which was then removed by suction filtration, and air dried. Yield was 120.3 g (77.6%) of 2-thienylglyoxamide m.p. 84°–87° C.; ir (CH$_2$Cl$_2$) $\gamma_{N-H}$ 3410, 3520 $\gamma_{C=O}$ 1655, 1715 cm$^{-1}$.

EXAMPLE 2

2-THIENYLGLYOXYLIC ACID

Thiophene acyl cyanide was prepared as in Example 1 and treated similarly with concentrated hydrochloric acid. After stirring for one hour the reaction mixture was allowed to stand overnight. One liter of water was added, the aqueous solution was saturated with salt and the reaction product then extracted with ethyl acetate. Yield was 92.0 g (59.0%) of thienyl glyoxylic acid [m.p. 87°–90° C.; ir (CH$_2$Cl$_2$) $\gamma_{O-H}$ 2200–3700, $\gamma_{C=O}$ 1655, 1710 cm$^{-1}$].

I claim:

1. A process for preparing thienylglyoxyl compounds represented by the structure

wherein R represents hydrogen, a halogen, an alkyl group having from 1 to about 8 carbon atoms, a cycloalkyl group having from 1 to about 8 carbon atoms or any combination thereof, and wherein R$^1$ represents NH$_2$ or OH which comprises reacting a thiophene carboxylic acid chloride with aqueous sodium cyanide in an inert, water-immiscible solvent in the presence of a phase transfer catalyst to form a thiophene carboxylic acid cyanide and reacting said thiophene acid cyanide with a strong mineral acid at a temperature and for a time sufficient to form said compound.

2. The process of claim 1 wherein said temperature ranges from about 10° C. to about 40° C.

3. The process of claim 2 wherein said time ranges from about 2 to about 16 hours.

4. A process for preparing thienylglyoxylic acid which comprises reacting thiophene carboxylic acid chloride with aqueous sodium cyanide in methylene chloride solvent and in the presence of a phase transfer catalyst to form thiophene carboxylic acid cyanide and then reacting said thiophene carboxylic acid cyanide with concentrated hydrochloric acid at a temperature and for a time sufficient to form thienylglyoxylic acid.

5. The process of claim 4 wherein said temperature ranges from about 20° C. to about 60° C.

6. The process of claim 5 wherein said time is about 16 hours.

7. A process for preparing thienylglyoxamide which comprises reacting thiophene carboxylic acid chloride with aqueous sodium cyanide in methylene chloride solvent and in the presence of a phase transfer catalyst to form thiophene carboxylic acid cyanide and reacting said thiophene carboxylic acid cyanide with concentrated hydrochloric acid at a temperature and for a time sufficient to form thienylglyoxamide.

8. The process of claim 7 wherein said temperature ranges from about 10° C. to about 40° C.

9. The process of claim 8 wherein said time is about 2 hours.

* * * * *

UNITED STATES PATENT AND TRADEMARK OFFICE
CERTIFICATE OF CORRECTION

PATENT NO. : 4,234,737

DATED : November 18, 1980

INVENTOR(S) : James M. Photis

It is certified that error appears in the above-identified patent and that said Letters Patent are hereby corrected as shown below:

Col. 1, line 35 - In the diagram over the arrow

" Zn, Hcl ⟶ " should be --  --.

Col. 1, line 62 - In the diagram add "C=O" to the carboxyl group.

" [diagram] " should be -- 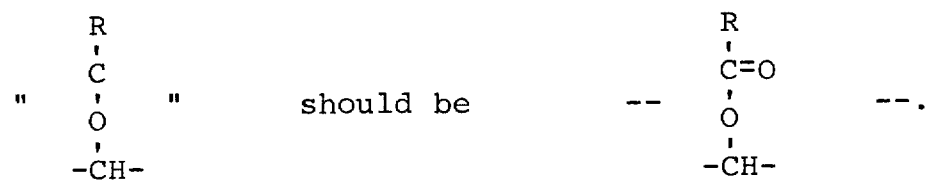 --.

Col. 2, line 3 - In the diagram add "C=O" to the carboxyl group.

" [diagram] " should be -- 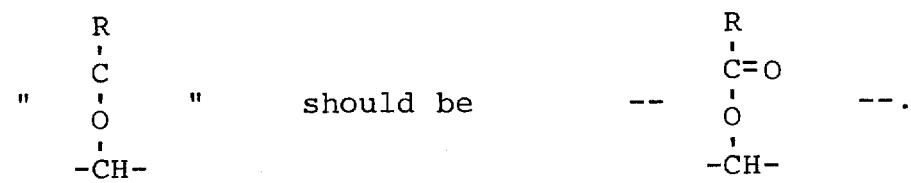 --.

Col. 2, line 43 - In the diagram after the thiophene ring $$-CH_2 - \overset{O}{\underset{\parallel}{C}} - Cl \longrightarrow$$ " should be -- 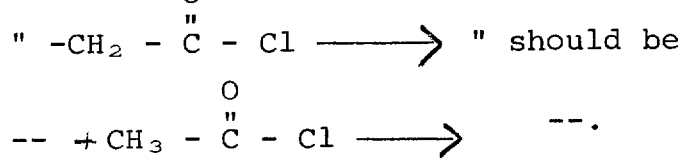 --.

UNITED STATES PATENT AND TRADEMARK OFFICE
CERTIFICATE OF CORRECTION

PATENT NO. : 4,234,737

DATED : November 18, 1980

INVENTOR(S) : James M. Photis

It is certified that error appears in the above-identified patent and that said Letters Patent are hereby corrected as shown below:

Col. 2, lines 48-49 - A parenthesis should be added around $$-- \xrightarrow[\begin{pmatrix}HCl\\NaNO_2\end{pmatrix}]{HNO_2} --.$$

Col. 4, line 47 - "catalysts" should be -- catalysis --.

Col. 5, line 3 - "wellunderstood" should be -- well-understood --.

Signed and Sealed this

Tenth Day of March 1981

[SEAL]

Attest:

RENE D. TEGTMEYER

Attesting Officer

Acting Commissioner of Patents and Trademarks